(12) United States Patent
Dionisio

(10) Patent No.: US 7,175,814 B2
(45) Date of Patent: Feb. 13, 2007

(54) AIR DISINFECTING SYSTEM AND CARTRIDGE DEVICE CONTAINING ULTRAVIOLET LIGHT

(76) Inventor: James L. Dionisio, 9801 Blue Lake Dr., Folsom, CA (US) 95630

( * ) Notice: Subject to any disclaimer, the term of this patent is extended or adjusted under 35 U.S.C. 154(b) by 406 days.

(21) Appl. No.: 10/461,313

(22) Filed: Jun. 16, 2003

(65) Prior Publication Data

US 2006/0263272 A1    Nov. 23, 2006

(51) Int. Cl.
*A61L 9/00* (2006.01)

(52) U.S. Cl. .............. 422/121; 422/42; 422/28; 422/123; 250/455.11; 96/224

(58) Field of Classification Search ............ 422/24, 422/120, 4, 121, 123, 28; 96/224; 250/435, 250/455.11
See application file for complete search history.

(56) References Cited

U.S. PATENT DOCUMENTS

| 2,279,810 | A |   | 4/1942  | Arnott |
|---|---|---|---|---|
| 2,732,501 | A |   | 1/1956  | Blaeker |
| 3,094,400 | A |   | 6/1963  | Blanton |
| 3,576,593 | A |   | 4/1971  | Circirello |
| 3,674,421 | A |   | 7/1972  | Decupper |
| 3,744,216 | A |   | 7/1973  | Halloran |
| 3,745,750 | A |   | 7/1973  | Arff |
| 3,757,495 | A |   | 9/1973  | Sievers |
| 3,768,970 | A |   | 10/1973 | Malmin |
| 3,798,879 | A |   | 3/1974  | Schmidt-Burbach et al. |
| 3,844,741 | A |   | 10/1974 | Dimitrik |
| 4,011,456 | A | * | 3/1977  | Bredewater et al. ..... 250/492.1 |
| 4,102,654 | A |   | 7/1978  | Pellin |
| 4,118,191 | A |   | 10/1978 | Bohnensieker |
| 4,210,429 | A | * | 7/1980  | Golstein ..................... 96/142 |
| 4,255,663 | A |   | 3/1981  | Lewis |
| 4,666,677 | A |   | 5/1987  | Ramus et al. |
| 4,750,917 | A |   | 6/1988  | Fujii |
| 4,931,654 | A |   | 6/1990  | Horng |
| 4,981,651 | A |   | 1/1991  | Horng |
| 5,185,015 | A |   | 2/1993  | Searle |
| 5,225,167 | A |   | 7/1993  | Wetzel |
| 5,259,062 | A | * | 11/1993 | Pelonis ..................... 392/365 |
| 5,334,347 | A |   | 8/1994  | Hollander |
| 5,492,557 | A |   | 2/1996  | Vanella |
| 5,523,057 | A |   | 6/1996  | Mazzilli |
| 5,558,158 | A |   | 9/1996  | Elmore |
| 5,607,647 | A |   | 3/1997  | Kinkead |
| 5,656,242 | A |   | 8/1997  | Morrow et al. |
| 5,730,770 | A |   | 3/1998  | Greisz |
| 5,853,676 | A |   | 12/1998 | Morgan, Jr. |
| 5,925,320 | A | * | 7/1999  | Jones ......................... 422/121 |

(Continued)

FOREIGN PATENT DOCUMENTS

DE      3637702      5/1998

*Primary Examiner*—Krisanne Jastrzab
*Assistant Examiner*—Sean E. Conley
(74) *Attorney, Agent, or Firm*—Gross & Associates

(57) ABSTRACT

A cartridge device containing UVC for air disinfection that comprises individual ultraviolet bulb, HEPA/Carbon filter, LED for detection of replacement, ballast and electrical components; cartridge is plugged into a backplane which allows for easy installation and servicing of all components. The backplane powers the device and can be encased in various configurations which can be used in multiple applications, including portable and permanent air treatment devices.

9 Claims, 4 Drawing Sheets

U.S. PATENT DOCUMENTS

| | | |
|---|---|---|
| 5,997,619 A | 12/1999 | Knuth et al. |
| 6,053,968 A | 4/2000 | Miller |
| 6,221,314 B1 | 4/2001 | Bigelow |
| 6,818,177 B1 * | 11/2004 | Turcotte .................... 422/24 |
| 6,939,397 B2 | 9/2005 | Nelsen et al. |
| 2004/0120845 A1 * | 6/2004 | Potember et al. ............. 422/4 |

* cited by examiner

AIR DISINFECTING SYSTEM AND CARTRIDGE DEVICE CONTAINING ULTRAVIOLET LIGHT

BACKGROUND OF THE INVENTION

1. Field of the Invention

This invention relates to air sterilization using ultraviolet light wave energy in a replaceable cartridge containing all electronic components as well as a High Efficiency Particulate Air Filter (HEPA) or Carbon filter, or a combination of the two.

2. Description of the Related Art

Indoor air quality has become a concern for residential and commercial buildings, airplanes, and cruise ships. Biological terrorism, SARS, sick buildings, cruise ship disease outbreaks, toxic molds, and epidemics of asthma and allergies have all made the issue of healthy air critical.

As indoor air quality grows to be a major concern, consumers are looking for a viable solution. The use of a HEPA filter is one solution, though these filters have limitations on their effectiveness. HEPA filtration only traps particles of 0.3 microns or greater and they are unable to kill viable pathogenic microorganisms. The use of a HEPA filter as the primary air decontamination device is not enough. Viruses, bacteria, mold spores, and allergens are small enough to bypass the filter and continue circulation through the indoor air.

Activated carbon filters are another common solution to improve indoor air quality. Carbon adsorbs odors while maintaining a low resistance to air flow. In addition, carbon filters are lightweight and durable and easy to install. However, carbon filtration is not effective in eliminating airborne particulates, viruses, bacteria, etc.

A current trend in air treatment devices is to use negatively charged ions to "cling" to the positively charged ions in the air in order to bring the particles to the floor for easy vacuuming. These products can be very misleading to the public claiming that the negatively charged ions are dispersed throughout the room when what is really being emitted is ozone. Ozone will freshen the air by eliminating odors, but is toxic and corrosive in large amounts. This type of product is normally accompanied by a disclaimer to see a physician before using the product.

Ultraviolet light is gaining popularity with many air treatment systems manufacturers because of its extremely high effectiveness in killing viable pathogenic microorganisms. Ultraviolet light is used in a number of portable air treatment systems and permanent ducting systems alike. However, the biggest problem with ultraviolet light is that it is extremely harmful to the eye when it is operating, which makes servicing the unit a difficult task. One may never know if the bulbs are working properly in their air treatment system because the owner is unable to look at the exposed bulbs to determine if they are still effective. As a result, many ultraviolet light systems are installed and never maintained. After a while, when the bulbs have lost their life, the system is ineffective. Therefore, an air treatment system utilizing the effective killing power of ultraviolet light that permits quick and simple maintenance is needed.

SUMMARY OF THE INVENTION

The present invention comprises an apparatus for decontaminating indoor air by exposing the air to ultraviolet light that is housed in a cartridge-base system that is easily unlocked from a backplane in which it is locked. The backplane can be of any dimension or shape, because the invention is the cartridge system itself. The present invention is designed to be implemented for commercial, residential, military, medical, personal or industrial use. The invention is designed in a way that it can be used in a portable stand-alone air treatment system, or installed into a fixed location, i.e., Heating, Ventilation and Air-Conditioning (HVAC) systems, airplanes, vehicles, vessels, etc.

The cartridge made in accordance with the present invention is the solution to the maintenance issues that come with conventional ultraviolet light air disinfection systems. The cartridge includes the benefits of HEPA and/or Carbon filtration along with the killing power of ultraviolet light in one all-inclusive component. The cartridge is cylindrical in shape and contains a single ultraviolet bulb directly in the center. The cartridge is plugged into a backplane by means of a power connection on the outside of the cartridge that is inserted into a power receptacle in the backplane. The cartridge can be from 3 to 24 inches in diameter, depending on the application. The cartridge has an air inlet on one end, and an air outlet on the opposite end. Air will be drawn into the cartridge by an impeller fan mounted in the preferred device for application. The air is first drawn through the HEPA/Carbon filter eliminating any odors and particulates of over 0.3 microns. The air is then drawn through the body of cartridge where the air is disinfected by the ultraviolet light. On the outside of the cartridge a Light Emitting Diode (LED) indicator will signal if the Cartridge needs to be replaced. The cartridge is easily removed and locked back into place in a matter of seconds.

The embodiments of the invention in which the exclusive property or privilege is claimed are a cartridge device used for disinfecting air which comprises a cylindrical housing dimensioned to be between 5 to 72 inches in length having a diameter between 3 and 24 inches, wherein the cartridge is fabricated from a light weight, durable high impact heat resistant material and the cartridge system is easily inserted or removed from the backplane via male receptacle on cartridge into female receptacle on the backplane; an ultraviolet bulb used for killing viable pathogenic microorganisms, wherein the ultraviolet light is at a wavelength from approximately 100 nanometers to approximately 325 nanometers; an integrated HEPA or Carbon filter, alone or in combination, for trapping particulates; a reflective coating on the inside of the cartridge to reflect the ultraviolet light, wherein the internal surface of the cartridge is coated with a highly reflective material or metallic compound such as clear specular aluminum to reflect the ultraviolet rays through all internal surfaces of the cartridge therein sterilizing up to 100% of the particulates in the stream of air flowing through said cartridge; a ballast that supplies power to the ultraviolet bulb; an LED indicator light on the outside of the cartridge; electrical components supplying power to the LED light, wherein the electrical power is supplied to the ballast via an electrical connection between the cartridge and the backplane; an air inlet disposed on one end of the cartridge; an air outlet disposed on the opposite end of the cartridge, wherein the air inlet and the air outlet of the cartridge ranges from 3 inch to 24 inches in diameter; and a plurality of seals around the air inlet and outlet.

BREIF DESCRIPTION OF THE DRAWINGS

Various exemplary embodiments of this invention will be described in detail, with reference to the following figures, wherein.

DETAILED DESCRIPTION OF THE INVENTION

Figure 1:
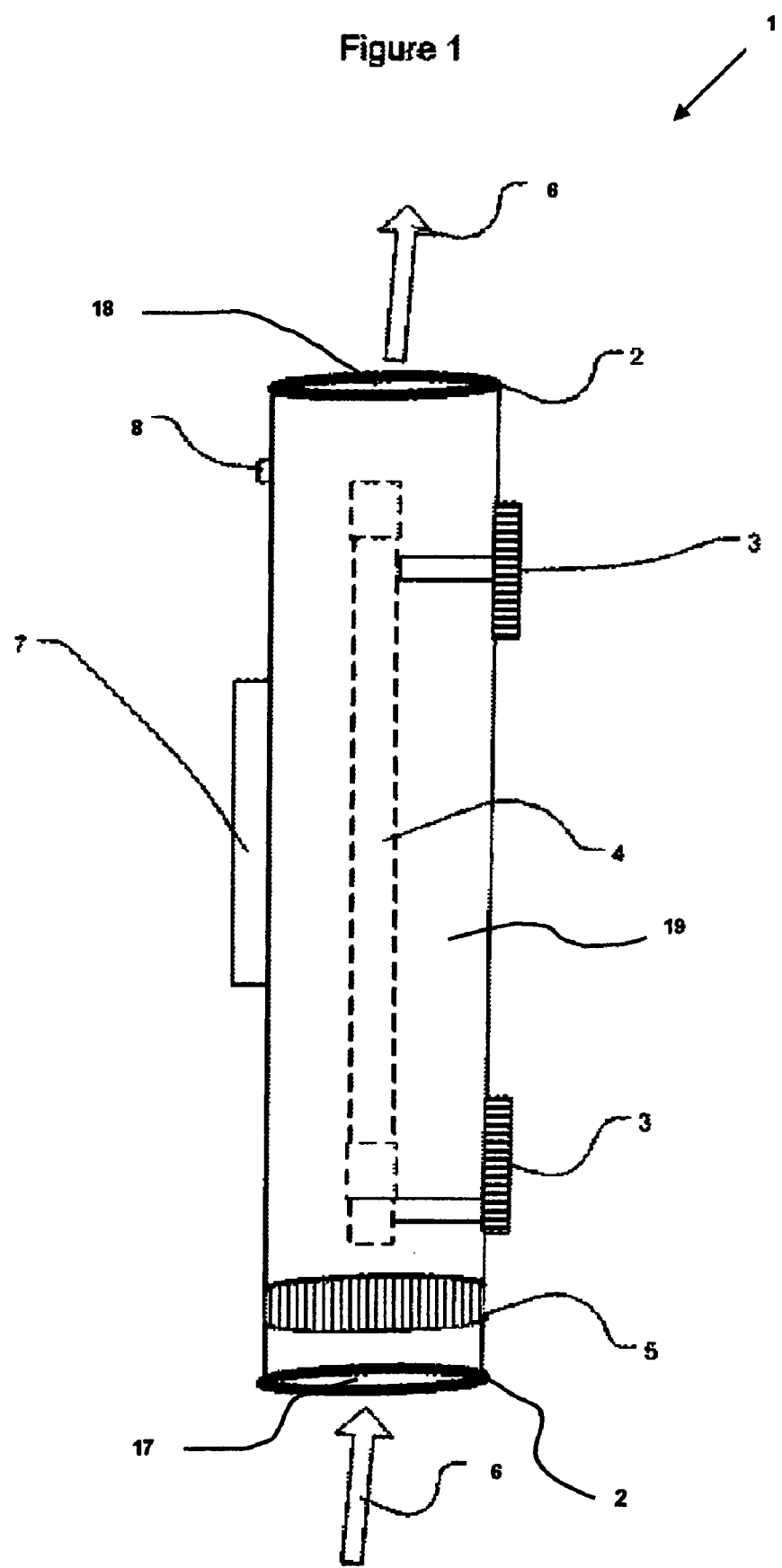
FIG. 1 is a front view of a cartridge standing alone made in accordance with the present invention.

The present invention comprises a cartridge device 1, as shown in FIG. 1, operably configured for easy removal from an encasement 14, wherein the cartridge 1 eliminates odors, particulates of over 0.3 microns and airborne pathogenic micro-organisms. The present invention further includes an air disinfecting system 30, wherein the air disinfecting system 30 includes the cartridge device 1 and the encasement 14. Referring more specifically to the drawings, wherein like reference numbers refer to like elements throughout the figures, the present invention is generally shown in FIG. 1.

Figure 4:
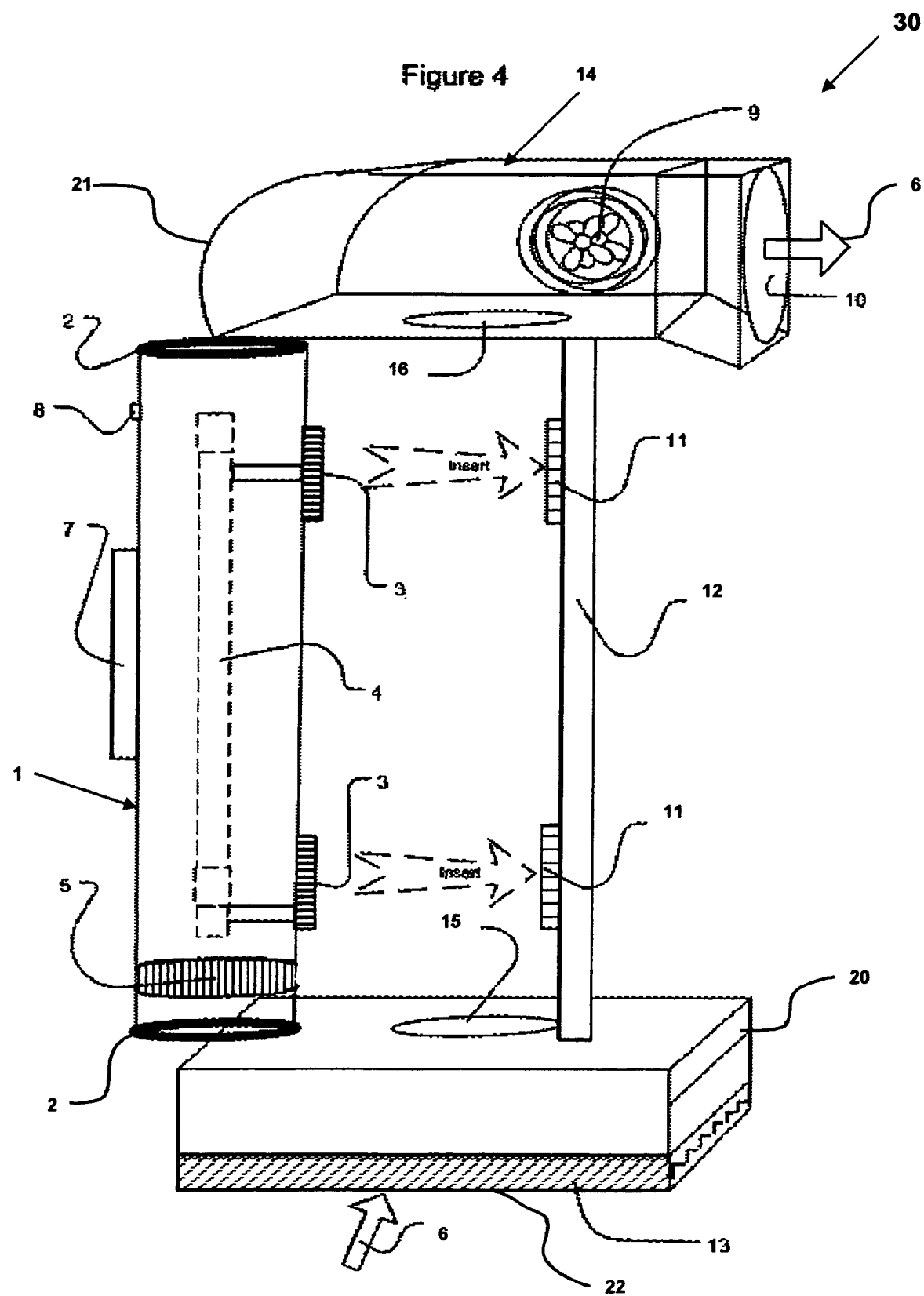

The cartridge 1 comprises a cartridge inlet 17, cartridge outlet 18, a cartridge chamber 19, a filter 5 and an ultraviolet light bulb 4. Further the cartridge 1 has a generally cylindrical shape dimensioned between 5 and 72 inches in length and having a diameter between 3 and 24 inches. The cartridge 1 is designed to engage the encasement 14, as shown in FIG. 4. An air column 6 is passed through the filter 5, wherein the filter 5 is a circular High Efficiency Particulate Air Filter (HEPA) or Carbon filter, alone or in combination and into the cartridge chamber 19 where the air column 6 is then disinfected by an ultraviolet light bulb 4. The air column 6 enters at the cartridge inlet 17 and is terminated at the cartridge outlet 18 where the air column 6 leaves the cartridge device 1. The cartridge 1 in the preferred embodiment is constructed out of light weight, durable, high impact, heat resistant material.

The cartridge 1 further includes a Light Emitting Diode (LED) 8 and a reflective coating on the interior of the cartridge 1, wherein the LED 8 indicates the need for a bulb change. The reflective coating reflects the ultraviolet rays from the ultraviolet light bulb 4. The reflective coating in the preferred embodiment is clear specular aluminum. However, it should be appreciated that in other various exemplary embodiments, other reflective coatings common in the art may be used.

Figure 3:
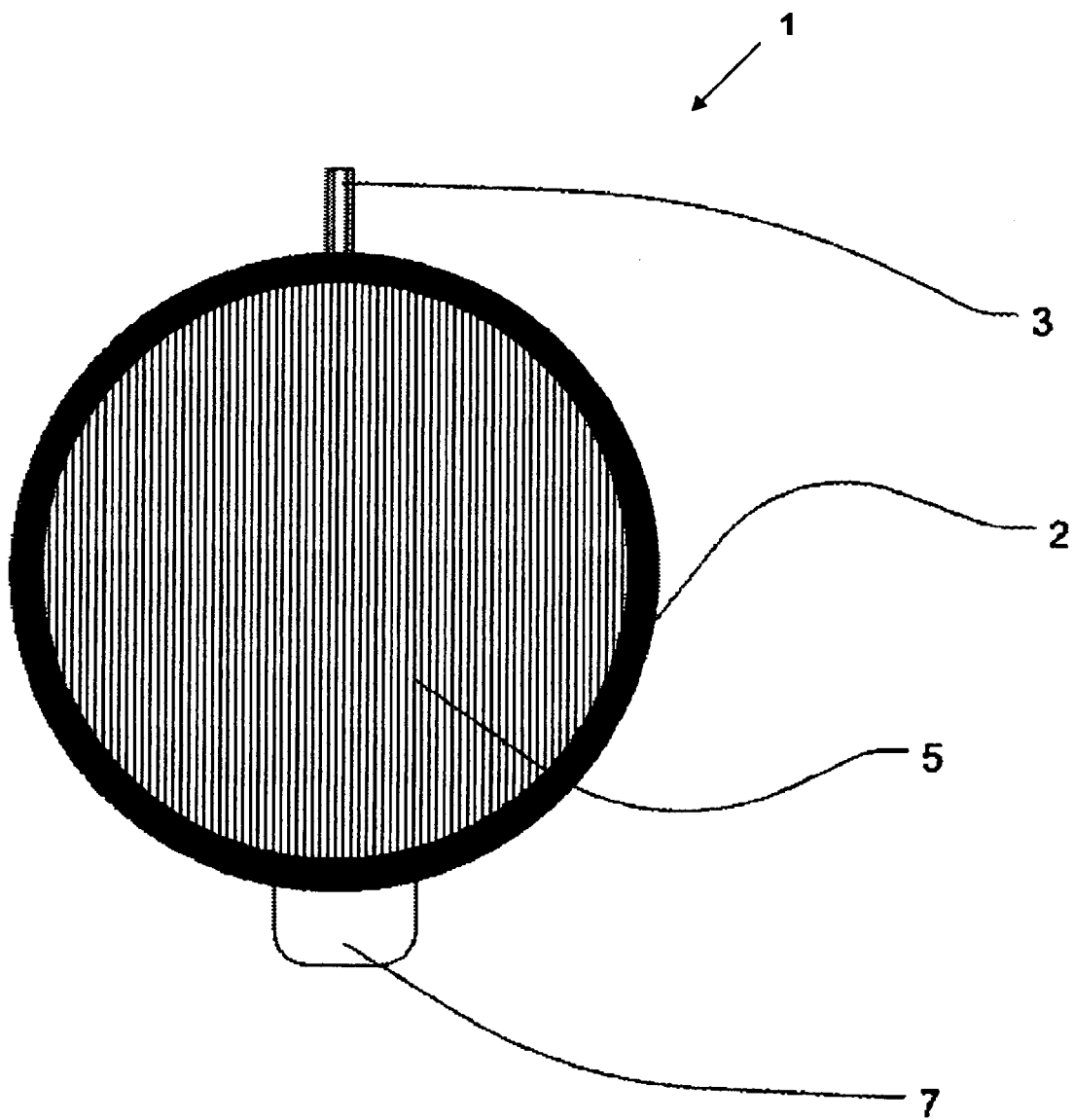
FIG. 3 is a bottom view of the cartridge through the air inlet of the device in FIG. 1; and, FIG. 4 is an exploded perspective view of the cartridge made in accordance with this invention and an encasement for the cartridge.

The filter 5 is located within the cartridge inlet 17 as shown in FIGS. 1 and 3. In the present invention the filter 5 is located approximately 1 inch above the cartridge inlet 17. The filter 5 captures large dust particles that are normally circulated through indoor air. Anything less than 0.3 microns in size (bacteria, viruses, some mold spores and allergens) will escape through the filter 5 and enter the cartridge device 1.

Figure 2:
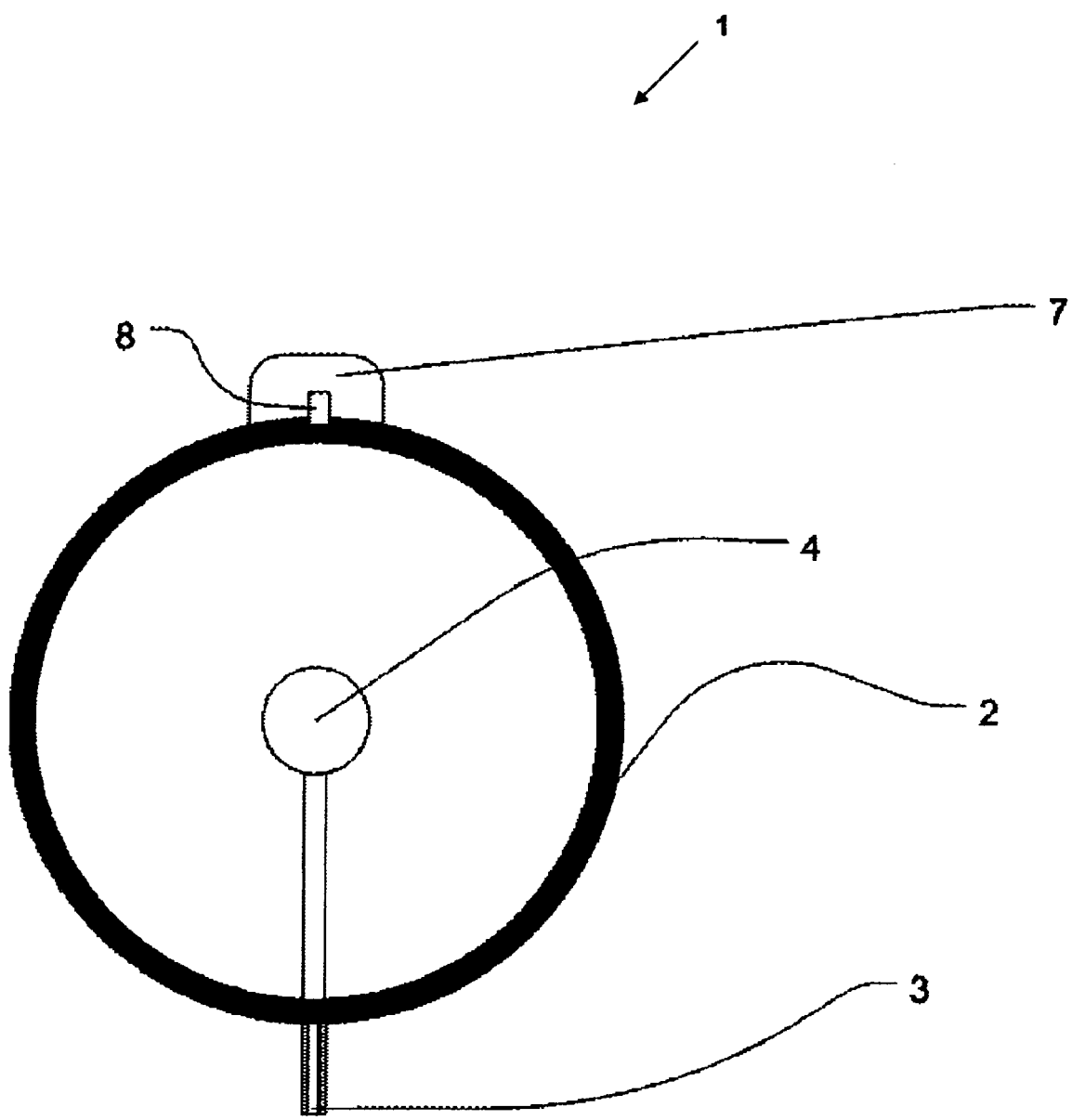
FIG. 2 is a top view of the cartridge through the air outlet of the device in FIG. 1.

Referring to FIGS. 1, 2 and 3, the ultraviolet light bulb 4 is disposed directly in the center of the cartridge 1 along the longitudinal axis, assuring that all air and particulates in the air column 6 entering the cartridge 1 will be sufficiently exposed to the ultraviolet light bulb 4. In the preferred embodiment, the ultraviolet light bulb 4 has a wavelength from approximately 100 nanometers to approximately 325 nanometers.

The cartridge 1 further includes a ballast or electronic pack 7, a plurality of power connections 3 and a plurality of seals 2, wherein the electronic pack 7 supplies electrical power to the ultraviolet light bulb 4. The ballast/electronic pack 7 and the power connections are disposed on the exterior of the cartridge 1, wherein the ballast 7 is disposed on the exterior of the cartridge 1 on the opposite side from the power connection 3. The power connection 3 is a male type connection and plugs into a female type connection in the encasement 14, completing a circuit, and supplying power to the LED light 8. The male electrical connectors 3, when engaged with the female connectors on the encasement 14 plug the cartridge 1 to the encasement 14. The seals 2 are disposed on the cartridge inlet 17 and cartridge outlet 18 such that the seals 2 in combination with the power connections 3, lock the cartridge 1 into the encasement 14, as shown in FIG. 4, creating an air-tight fit. In the present embodiment the seals 2 are rubber.

In the preferred embodiment of the invention, as shown in FIG. 4, the cartridge 1 is disposed vertically within the encasement 14, with the cartridge inlet 17 facing downward and the cartridge outlet 18 facing upward, as shown in FIG. 4. The encasement 14 includes a base member 20, a top member 21 and a backplane 12. The base member 20 includes a pre-filter 13 and first and second airflow orifices 15 and 22. The top member 21 includes an impeller fan 9, an outlet orifice 16 and an exhaust orifice 10. The impeller fan 9 is disposed in the top member 21 of the encasement 14 drawing the air upward and creating the air column 6, through the pre-filter 13, the airflow orifice 15, and the filter 5. The air column 6 is then pulled into the chamber 19 of the cartridge 1 where all airborne particulates are penetrated by the ultraviolet light bulb 4 the required amount of time resulting in a kill rate of 100% for almost all bacteria and viruses. In the present invention the required amount of time is approximately 5 seconds. The air column 6 continues out of the cartridge 1 through the exhaust orifice 10 with little or no traceable contaminants.

The intensity of the ultraviolet light bulb 4 and the dwell time of the air column 6 in the cartridge chamber 19 are predetermined based on the type and concentration of the pathogenic micro-organisms in the air column 6. Different exposures to ultraviolet light are required to kill different micro-organisms; likewise, the higher the intensity bulb, and the closer the microorganism is to the bulb, the less dwell time required for effective kill. The following table presents a comparison between a conventional ultraviolet air treatment system, and the cartridge device 1 of the present invention using a 14 inch bulb:

| Organisms: | Energy dosage of Ultraviolet radiation in microwatts sec/cm2 needed for 100% kill factor | Approximate exposure time (in seconds) necessary to achieve 100% kill factor in a regular ultraviolet air treatment system | Approximate exposure time (in seconds) necessary to achieve 100% kill factor in 5 inch diameter UVBio-Clean Cartridge |
|---|---|---|---|
| Bacteria: | | | |
| Bacillus Anthracis-Anthrax | 8,700 | 10.8 | 1.2 |
| Bacillus Magaterium sp. (spores) | 5,200 | 6.5 | 1.7 |
| Bacillus paratyphusus | 6,100 | 7.6 | 2 |
| Bacillus subtilis spores | 22,000 | 27.5 | 7.5 |
| Bacillus subitilis | 11,000 | 13.7 | 3.7 |
| Cornebacterium diphtheriae | 6,510 | 8.1 | 2.2 |
| Ebertelia typhosa | 4,100 | 5.1 | 1.4 |
| Escherichia coli | 6,600 | 8.3 | 2.2 |
| Leptospiracanicola-infectious Jaundice | 6,000 | 7.5 | 2 |

-continued

| Organisms: | Energy dosage of Ultraviolet radiation in microwatts sec/cm2 needed for 100% kill factor | Approximate exposure time (in seconds) necessary to achieve 100% kill factor in a regular ultraviolet air treatment system | Approximate exposure time (in seconds) necessary to achieve 100% kill factor in 5 inch diameter UVBio-Clean Cartridge |
|---|---|---|---|
| Microccoucus candidus | 12,300 | 15.4 | 4.2 |
| Microccoucus sphaeroides | 15,400 | 19.3 | 5.2 |
| Mycobacterium tuberculosis | 10,000 | 12.5 | 3.4 |
| Pseudomonas aeruginosa | 10,500 | 13.0 | 3.6 |
| Pseudomonas florescens | 6,600 | 8.3 | 2.2 |
| Salmonella enteritidis | 7,600 | 9.5 | 2.6 |
| Salmonela paratyphi-Enteric Fever | 6,100 | 7.6 | 2 |
| Salmonella typhosa-Typhoid Fever | 4,100 | 5.1 | 1.4 |
| Shigella dyseteriae-Dysentery | 4,200 | 5.2 | 1.4 |
| Shigella flexneri-Dysentery | 3,400 | 4.3 | 1.1 |
| Vibrio comma-Cholera | 6,500 | 8.1 | 2.2 |
| Virus: | | | |
| Bacteriopfage-E.Coli | 6,600 | 8.3 | 2.2 |
| Infectious Hepatitis | 8,000 | 10.0 | 2.7 |
| Influenza | 6,600 | 8.3 | 2.2 |
| Molds: | | | |
| Aspergillius flavus | 99,000 | 123.8 | 34 |
| Aspergilius glaucus | 88,000 | 110.0 | 30.2 |
| Aspergilius niger | 330,000 | 412.5 | 113.5 |
| Penicilium expansum | 22,000 | 27.5 | 7.5 |
| Penicilium roqueforti | 26,400 | 33.0 | 9 |
| Penicilim digitatum | 88,000 | 110.0 | 30.2 |

As presented in the above table, the cartridge device 1 is more effective in achieving a 100% kill rate of airborne micro-organisms. Here are the reasons why: Because the cartridge device 1 of the present invention is an enclosed cartridge, the air column 6 is forced to fully encompass the length of the ultraviolet light bulb 4, which can be up to 75 inches in length. In the cartridge device 1, the air column 6 will always be within 0–10 inches away from the bulb 4 for the required amount of time to destroy 100% of microorganisms. In the present invention required time is approximately 5 seconds. In a conventional ultraviolet air treatment system, the ultraviolet bulbs are not contained in an enclosed capsule like the cartridge 1 and the air is generally passed perpendicularly to the bulb anywhere from 1 to 3 feet away. Therefore, the micro-organisms that pass through the conventional system are not fully exposed to the ultraviolet light for a significant length of time at a close distance, which are the main components for 100% kill factor.

It is to be noted that more resistant micro-organisms, such as mold, that are not killed with the initial exposure to the ultraviolet light bulb 4 will eventually be destroyed as the micro-organisms continues circulation through the device 1.

Although the presented invention has been described in detail throughout this document, it should be understood that many variations and/or modifications of the basic inventive concept will still fall within the spirit and scope of the present invention as defined in the appended claims.

What is claimed is:

1. An air disinfecting system comprising:
a cartridge, having a length and a diameter, and interior chamber, an airflow inlet, an airflow outlet, a longitudinal axis, an ultraviolet light bulb disposed in the chamber and along the longitudinal axis of the cartridge, a filter disposed radially along the longitudinal axis within the chamber, a reflective coating disposed on the inside of the chamber, a ballast that supplies power to the ultraviolet light bulb, and an electrical connector disposed on the exterior of the cartridge and electrically connected to the ballast; and,
an encasement, wherein the encasement includes, a base member having a first and second airflow orifice, a backplane disposed on the base member, a top member having an outlet orifice and an exhaust orifice and being disposed on the backplane, wherein the backplane is operably configured to receive the electrical connector of the cartridge and the cartridge inlet and outlet are axially aligned with the second airflow orifice of the base member and the outlet orifice of the top member, an impeller and electrical connections to supply electrical power to the impeller and the cartridge.

2. An air disinfecting system of claim 1, wherein the length and diameter of the cartridge have a ration of 3:1.

3. An air disinfecting system as recited in claim 1, wherein the cartridge includes a seal around the airflow inlet and outlet.

4. An air disinfecting system of recited in claim 1, wherein the cartridge is fabricated from a light weight, durable, high impact, heat resistant material.

5. An air disinfecting system of recited in claim 1, wherein the electrical connector on the cartridge is a male type connector.

6. An air disinfecting system comprising:
a cartridge having a length and a diameter, wherein the length and diameter have a ratio of 3:1, an interior chamber, an airflow inlet, an airflow outlet, a longitudinal axis, an ultraviolet light bulb disposed in the chamber and along the longitudinal axis of the cartridge, a filter disposed radially along the longitudinal axis within the chamber, a reflective coating disposed on the inside of the chamber, a ballast that supplies power to the ultraviolet light bulb, and an electrical connector disposed on the exterior of the cartridge and electrically connected to the ballast; and,
an encasement, wherein the encasement includes, a base member having a first and second airflow orifice, a backplane disposed on the base member, a top member having an outlet orifice and an exhaust orifice and being disposed on the backplane, wherein the backplane is operably configured to receive the electrical connectors of the cartridge and the cartridge inlet and outlet are axially aligned with the second airflow orifice of the base member and the outlet orifice of the top member, an impeller and electrical connections to supply electrical power to the impeller and the cartridge.

7. An air disinfecting system as recited in claim 6, wherein the reflective coating of the cartridge is clear specular aluminum.

8. An air disinfecting system as recited in claim 6, the cartridge includes a seal around the airflow inlet and outlet.

9. An air disinfecting system as recited in claim 6, wherein the electrical connector on the cartridge is a male type connector.

* * * * *